United States Patent
Kobayashi et al.

(10) Patent No.: US 9,480,451 B2
(45) Date of Patent: Nov. 1, 2016

(54) X-RAY IMAGE PROCESSING APPARATUS, X-RAY DIAGNOSTIC APPARATUS, AND X-RAY IMAGE PROCESSING METHOD

(71) Applicant: Toshiba Medical Systems Corporation, Otawara-shi (JP)

(72) Inventors: Yoshimasa Kobayashi, Nasushiobara (JP); Shumpei Ohashi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 81 days.

(21) Appl. No.: 14/461,894

(22) Filed: Aug. 18, 2014

(65) Prior Publication Data

US 2015/0063541 A1 Mar. 5, 2015

(30) Foreign Application Priority Data

Sep. 2, 2013 (JP) ................................. 2013-181702

(51) Int. Cl.
```
A61B 6/00      (2006.01)
G06T 5/00      (2006.01)
H03H 17/02     (2006.01)
A61B 6/12      (2006.01)
G06T 5/20      (2006.01)
G06T 5/50      (2006.01)
A61B 18/14     (2006.01)
A61B 18/00     (2006.01)
```
(52) U.S. Cl.
CPC ............... *A61B 6/5258* (2013.01); *A61B 6/12* (2013.01); *A61B 6/4441* (2013.01); *A61B 6/487* (2013.01); *A61B 6/503* (2013.01); *A61B 6/5211* (2013.01); *G06T 5/002* (2013.01); *G06T 5/20* (2013.01); *G06T 5/50* (2013.01); *H03H 17/0213* (2013.01); *H03H 17/0255* (2013.01); *A61B 18/1492* (2013.01); *A61B 2018/00351* (2013.01); *G06T 2207/10116* (2013.01)

(58) Field of Classification Search
None
See application file for complete search history.

(56) References Cited

U.S. PATENT DOCUMENTS

| | | | | |
|---|---|---|---|---|
| 7,408,168 | B1 * | 8/2008 | Aufrichtig | G01T 1/29 250/370.09 |
| 2003/0210047 | A1 * | 11/2003 | Mitchell | G01R 33/4806 324/309 |
| 2008/0181478 | A1 * | 7/2008 | Maeda | G06K 9/40 382/128 |
| 2009/0290686 | A1 * | 11/2009 | Liu | H04N 5/3577 378/162 |
| 2010/0098216 | A1 * | 4/2010 | Dobson | G01T 1/00 378/104 |
| 2010/0119140 | A1 * | 5/2010 | Burns | G06T 5/10 382/132 |
| 2012/0275569 | A1 * | 11/2012 | Xue | A61B 6/4233 378/91 |
| 2013/0223717 | A1 * | 8/2013 | Reboni | G06T 7/0012 382/131 |
| 2013/0301801 | A1 * | 11/2013 | Liu | H05G 1/08 378/91 |

* cited by examiner

*Primary Examiner* — Utpal Shah
(74) *Attorney, Agent, or Firm* — Oblon, McClelland, Maier & Neustadt, L.L.P.

(57) ABSTRACT

An X-ray image processing apparatus according to an embodiment includes a specifying unit and a decision unit. The specifying unit processes a first X-ray image based on an output signal from an X-ray detector influenced by the action of an electromagnetic field, and specifies noise characteristics unique to noise components which are contained in the first X-ray image and originate from the action of the electromagnetic field on the X-ray detector. The decision unit decides filter characteristics for reducing the noise components which are contained in the first X-ray image and originate from the action of the electromagnetic field on the X-ray detector based on the specified noise characteristics.

11 Claims, 12 Drawing Sheets

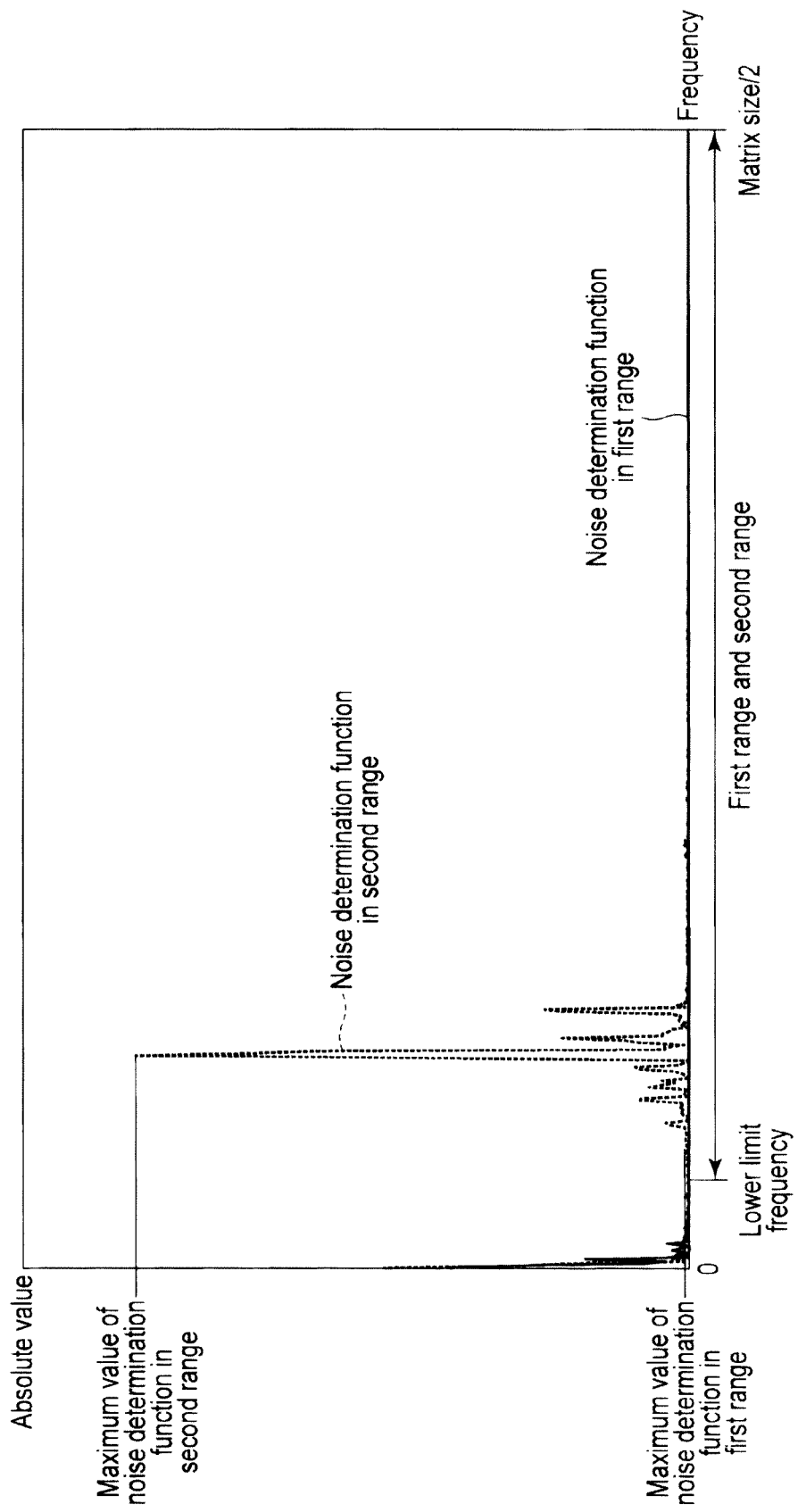
F I G. 8

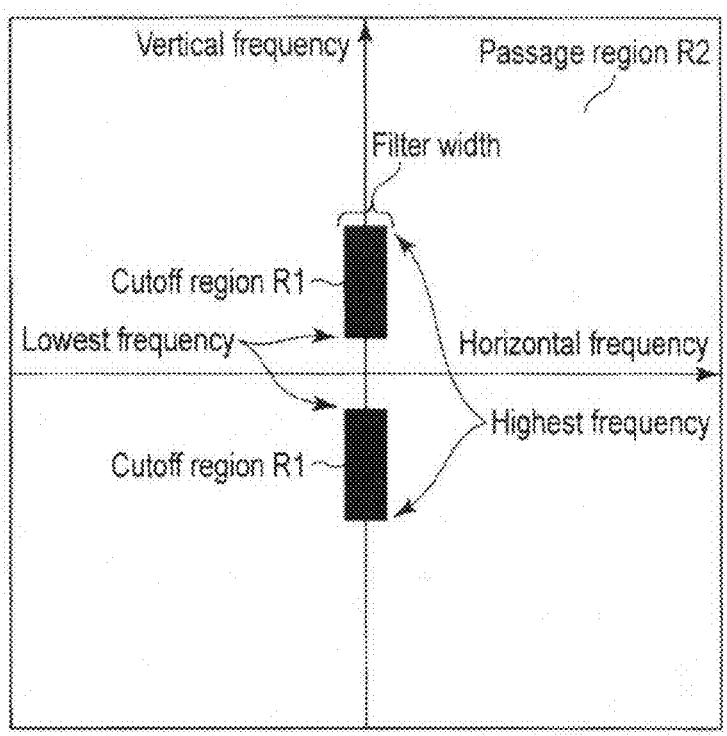
F I G. 10
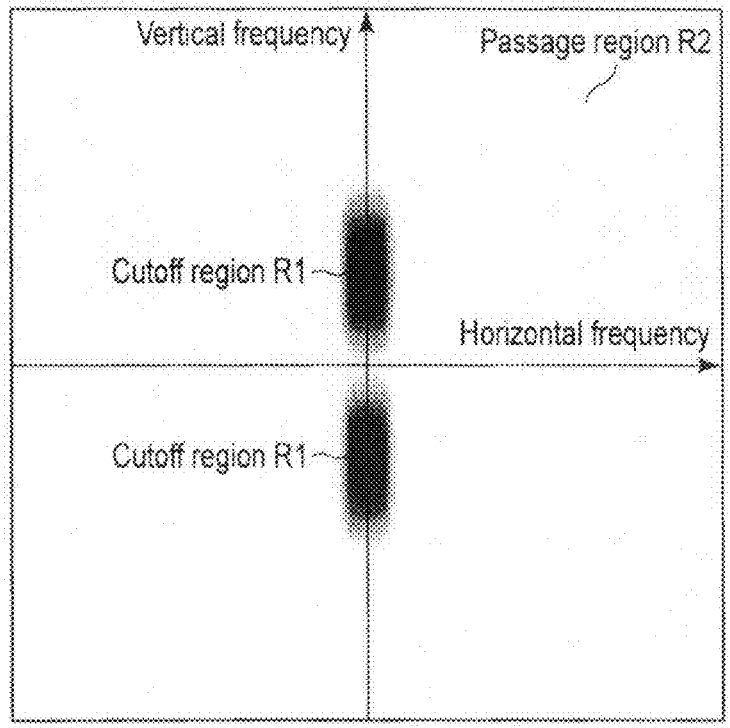
F I G. 11

X-RAY IMAGE PROCESSING APPARATUS, X-RAY DIAGNOSTIC APPARATUS, AND X-RAY IMAGE PROCESSING METHOD

CROSS-REFERENCE TO RELATED APPLICATIONS

This application is based upon and claims the benefit of priority from the prior Japanese Patent Application No. 2013-181702, filed Sep. 2, 2013 the entire contents of which are incorporated herein by reference.

FIELD

Embodiments described herein relate generally to an X-ray image processing apparatus, an X-ray diagnostic apparatus, and an X-ray image processing method.

BACKGROUND

There is available a catheter ablation treatment for treating arrhythmia, tachycardia, and the like. In a catheter ablation treatment, the operator searches for a site of occurrence of arrhythmia or an accessory pathway as a cause of tachycardia, and cauterizes part of the cardiac muscle by energizing the catheter electrode with high-frequency energy. Recently, as a navigation technique for moving the distal end of a catheter to a region to be cauterized, a mapping method is used, which generates a potential map simultaneously and three-dimensionally indicating morphological information and potential information of the heart by measuring the position of the distal end of the catheter electrode using an electromagnetic field.

However, when, for example, performing X-ray fluoroscopy while seeing a potential map, an FPD (Flat Panel Detector) as an X-ray detector of an X-ray diagnostic apparatus is exposed to an electromagnetic field. The image data acquired by the FPD is mixed with noise upon being influenced by the electromagnetic field generated from a system (to be referred to as a mapping system hereinafter) which executes the mapping method. A permalloy is placed in front of the FPD to reduce the influence of an electromagnetic field. However, the permalloy attenuates not only an electromagnetic field from the mapping system but also X-rays. In order to obtain an X-ray image with image quality similar to that obtained without using any permalloy, it is necessary to increase the X-ray irradiation dose.

It is an object to provide an X-ray image processing apparatus, an X-ray diagnostic apparatus, and an X-ray image processing method which can reduce noise on an X-ray image which is generated by the electromagnetic field generated by a mapping system which executes the mapping method.

BRIEF DESCRIPTION OF THE DRAWINGS

FIG. 8 is a graph showing an example of noise determination functions in the first and second ranges which are generated by the specifying unit FIG. 2;

FIG. 10 is a view showing an example of a noise reduction filter having the filter characteristics decided by a decision unit in FIG. 2;

FIG. 11 is a view showing an example of a noise reduction filter which smooths the boundary between a cutoff region and a passage region, which is generated by the decision unit in FIG. 2;

DETAILED DESCRIPTION

Figure 1:
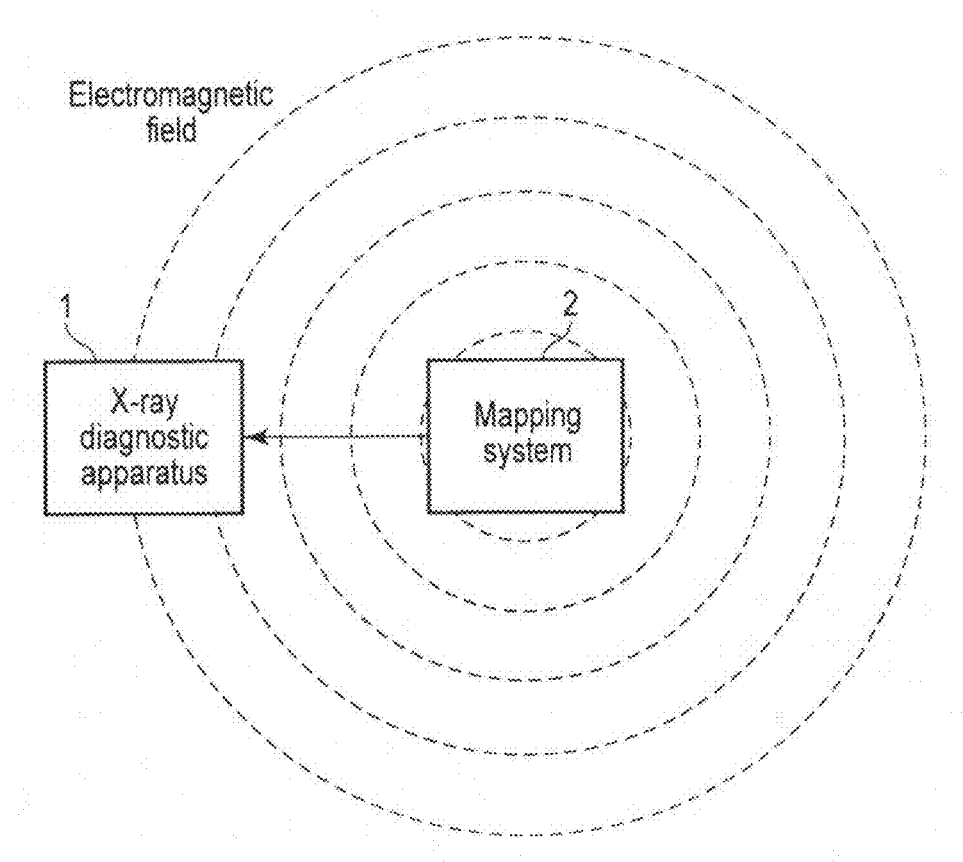
FIG. 1 is a view showing the connection between an X-ray diagnostic apparatus and a mapping system according to an embodiment.

An x-ray image processing apparatus according to an embodiment includes a specifying unit and a decision unit. The specifying unit processes a first X-ray image based on an output signal from an X-ray detector influenced by the action of an electromagnetic field, and specifies noise characteristics unique to noise components which are contained in the first X-ray image and originate from the action of the electromagnetic field on the X-ray detector. The decision unit decides filter characteristics for reducing the noise components which are contained in the first X-ray image and originate from the action of the electromagnetic field on the X-ray detector based on the specified noise characteristics.

An X-ray image processing apparatus, an X-ray diagnostic apparatus, and an X-ray image processing method according to an embodiment will be described below with reference to the accompanying drawing. Note that in the following description, the same reference numerals denote constituent elements having almost the same functions and arrangements, and a repetitive description will be made only when required.

FIG. 1 is a view showing the connection between an X-ray diagnostic apparatus 1 and a mapping system 2 according to this embodiment. Typically, the X-ray diagnostic apparatus 1 and the mapping system 2 are installed in the same operating room. The X-ray diagnostic apparatus 1 is connected to the mapping system 2 via a network. The mapping system 2 generates a potential map simultaneously and three-dimensionally indicating morphological information and potential information of the heart by measuring the position of the distal end of a catheter electrode using an electromagnetic field. The mapping system 2 transmits the potential map generated by the mapping method to the X-ray diagnostic apparatus 1. As will be described later, the electromagnetic field generated from the mapping system 2 acts on the X-ray diagnostic apparatus 1. The X-ray image generated by the X-ray diagnostic apparatus 1 under the action of the electromagnetic field is mixed with noise originating from the action of the electromagnetic field on the X-ray diagnostic apparatus 1.

Figure 2:
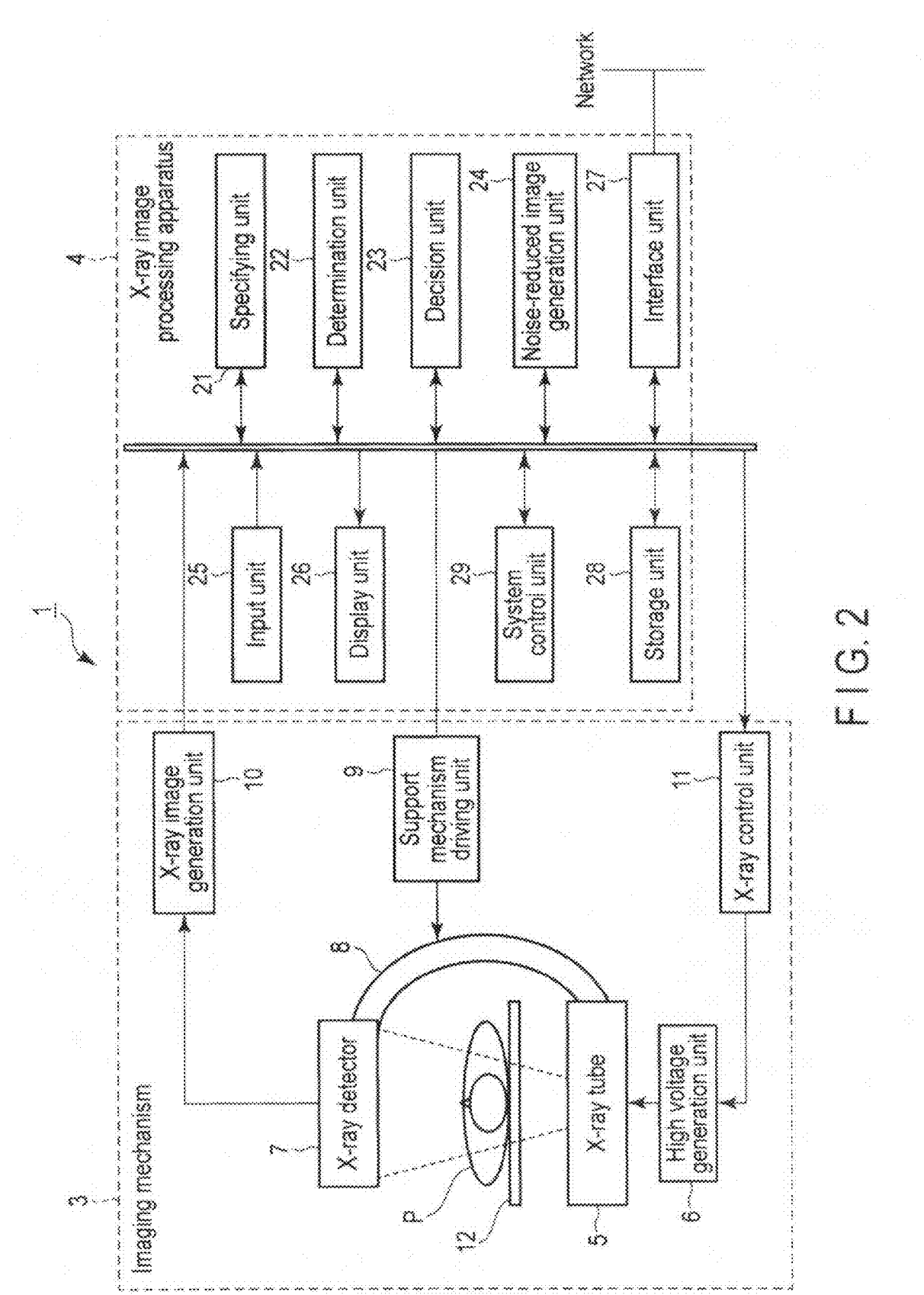
FIG. 2 is a block diagram showing the arrangement of an X-ray diagnostic apparatus according to this embodiment.

FIG. 2 is a block diagram showing the arrangement of the X-ray diagnostic apparatus 1 according to this embodiment. The X-ray diagnostic apparatus 1 includes an imaging mechanism 3 and an X-ray image processing apparatus 4. The imaging mechanism 3 includes an X-ray tube 5, a high voltage generation unit 6, an X-ray detector 7, a support mechanism 8, a support mechanism driving unit 9, an X-ray image generation unit 10, and an X-ray control unit 11.

The X-ray tube 5 is connected to the high voltage generation unit 6. The high voltage generation unit 6 generates a tube voltage applied to the X-ray tube 5. The X-ray tube 5 generates X-rays upon reception of a tube voltage and a filament current from the high voltage generation unit 6. The high voltage generation unit 6 applies a tube voltage in accordance with a control signal from the X-ray control unit 11. The high voltage generation unit 6 supplies a filament current in accordance with a control signal from the X-ray control unit 11.

The X-ray detector 7 detects the X-rays generated by the X-ray tube 5 and transmitted through an object P. The X-ray detector 7 is implemented by, for example, an FPD (Flat Panel Detector). The FPD has a photoelectric conversion film which converts light into an electrical signal. The photoelectric conversion film converts incident X-rays into an electrical signal. The electrical signal generated by the photoelectric conversion film is output to an A/D converter (Analog to Digital converter) (not shown). The A/D converter converts an electrical signal into digital data. The A/D converter outputs the digital data to the X-ray image generation unit 10.

Although described in detail later, the X-ray detector 7 is exposed to the electromagnetic field generated by the mapping system 2. The X-ray image generated by the X-ray image generation unit 10 contains noise components originating from the action of the electromagnetic field generated by the mapping system 2 on the X-ray detector 7. The noise components will be referred to as electromagnetic field noise.

The support mechanism 8 movably supports the X-ray tube 5 and the X-ray detector 7. More specifically, the support mechanism 8 includes, for example, a C-arm and a C-arm support portion (neither of which is shown). The X-ray tube 5 and the X-ray detector 7 are mounted on the C-arm so as to face each other.

The support mechanism driving unit 9 drives the support mechanism 8 under the control of a system control unit 29 (to be described in detail later). More specifically, the support mechanism driving unit 9 supplies a driving signal to the C-arm support portion in accordance with a control signal from the X-ray control unit 11 to slide and rotate the C-arm in a predetermined direction. At the time of an X-ray diagnosis, the object P placed on a top 12 is arranged between the X-ray tube 5 and the X-ray detector 7. The top 12 is movably supported by a bed in accordance with an instruction from the operator via an input unit 25 (to be described later).

The X-ray image generation unit 10 generates an X-ray image by preprocessing the digital data output from the X-ray detector 7. The preprocessing includes, for example, sensitivity nonuniformity correction between channels in the X-ray detector 7 and correction concerning signal omission. The X-ray image generation unit 10 outputs the generated X-ray image to a specifying unit 21. Note that the X-ray image generation unit 10 may output the generated X-ray image to a storage unit 28 (to be described later).

The X-ray image processing apparatus 4 includes the specifying unit 21, a determination unit 22, a decision unit 23, a noise-reduced image generation unit 24, the input unit 25, a display unit 26, an interface unit 27, the storage unit 28, and the system control unit 29.

The specifying unit 21 processes an X-ray image to specify noise characteristics unique to electromagnetic field noise originating from the action of the electromagnetic field generated by the mapping system 2 on the X-ray detector 7. The decision unit 23 uses the noise characteristics to decide the filter characteristics of a filter (to be referred to as a noise reduction filter hereinafter) for reducing electromagnetic field noise. In addition, the determination unit 22 uses the noise characteristics to determine whether to apply the noise reduction filter.

The determination unit 22 decides, based on the noise characteristics specified by the specifying unit 21, whether to apply the noise reduction filter to an X-ray image.

The decision unit 23 decides filter characteristics for reducing noise components based on the noise characteristics specified by the specifying unit 21.

The noise-reduced image generation unit 24 generates an X-ray image with reduced electromagnetic field noise components by applying the noise reduction filter having the filter characteristics decided by the decision unit 23 to the X-ray image. An X-ray image with reduced electromagnetic field noise components will be referred to as an electromagnetic field noise reduced image hereinafter.

The input unit 25 inputs X-ray conditions, an X-ray imaging position, X-ray fluoroscopy position, the start and end of X-ray imaging or X-ray fluoroscopy, and the like, which are desired by the operator. The input unit 25 inputs various instructions, commands, information, selections, and settings from the operator to the system control unit 29. The input unit 25 includes input devices such as a trackball, switch buttons, mouse, mouse wheel, and keyboard. Note that the input device may be a touch panel covering the display screen of the display unit 26.

The display unit 26 displays various types of information of X-ray images and the like. For example, the display unit 26 displays an electromagnetic field noise reduced image. The display unit 26 may also display a potential map input from the mapping system 2 via the interface unit 27 (to be described later). Note that the display unit 26 may display an X-ray image to which the noise reduction filter is not applied.

The interface unit 27 is connected to the mapping system 2, a PACS (Picture Archiving and Communication Systems), and other computers via network. The interface unit 27 receives a potential map from the mapping system 2. The received potential map is output to the display unit 26.

The storage unit 28 stores operator instructions supplied from the input unit 25 (to be described later). For example, the storage unit 28 stores a lower limit frequency, a determination constant, a noise threshold, and a filter width. Note that the lower limit frequency, the noise threshold, and the filter width may be changed in accordance with instructions from the operator via the input unit 25. Note that the storage unit 28 may store a program (to be referred to as a noise reduction processing program hereinafter) for generating an electromagnetic field noise reduced image.

The system control unit 29 functions as the main unit of the X-ray diagnostic apparatus 1 according to this embodiment. The system control unit 29 reads out the noise reduction processing program from the storage unit 28 and expands the program. The system control unit 29 then comprehensively controls the respective units of the X-ray diagnostic apparatus 1 in accordance with the noise reduction processing program. Electromagnetic field noise reduction processing is executed by this comprehensive control.

Electromagnetic field noise reduction processing performed under the control of the system control unit 29 will be described below. In order to give a concrete description below, a catheter ablation treatment using the X-ray diagnostic apparatus 1 and the mapping system 2 will be described as a concrete example.

A catheter ablation treatment is one of the cardiac treatment techniques. The catheter ablation treatment is a technique of searching for a site of occurrence of arrhythmia or an accessory pathway as a cause of tachycardia and cauterizing part of the cardiac muscle by energizing the electrode provided in the electrode catheter with high-frequency energy. The mapping system 2 detects the position of the electrode by using an electromagnetic field. The mapping system 2 generates a potential map based on the detected position of the electrode and the potential detected by the electrode. The potential map is an image simultaneously and three-dimensionally indicating the morphological information and potential information of the heart. A method of generating such a potential map is called a mapping method.

On the other hand, in a catheter ablation treatment, the X-ray diagnostic apparatus performs X-ray fluoroscopy. X-ray fluoroscopy generates an X-ray image in real time. The user moves the electrode catheter to a region to be cauterized while observing a potential map and an X-ray image, and cauterizes the region to be cauterized by operating the electrode catheter.

As described above, the mapping system 2 which executes the mapping method generates an electromagnetic field. The X-ray diagnostic apparatus 1 is installed in the operating room where the mapping system 2 is installed. The X-ray detector 7 of the X-ray diagnostic apparatus 1 is therefore under the action of the electromagnetic field generated by the mapping system 2. The X-ray image acquired by the X-ray detector 7 under the action of the electromagnetic field contains electromagnetic field noise originating from the action of the electromagnetic field on the X-ray detector 7.

Figure 3:
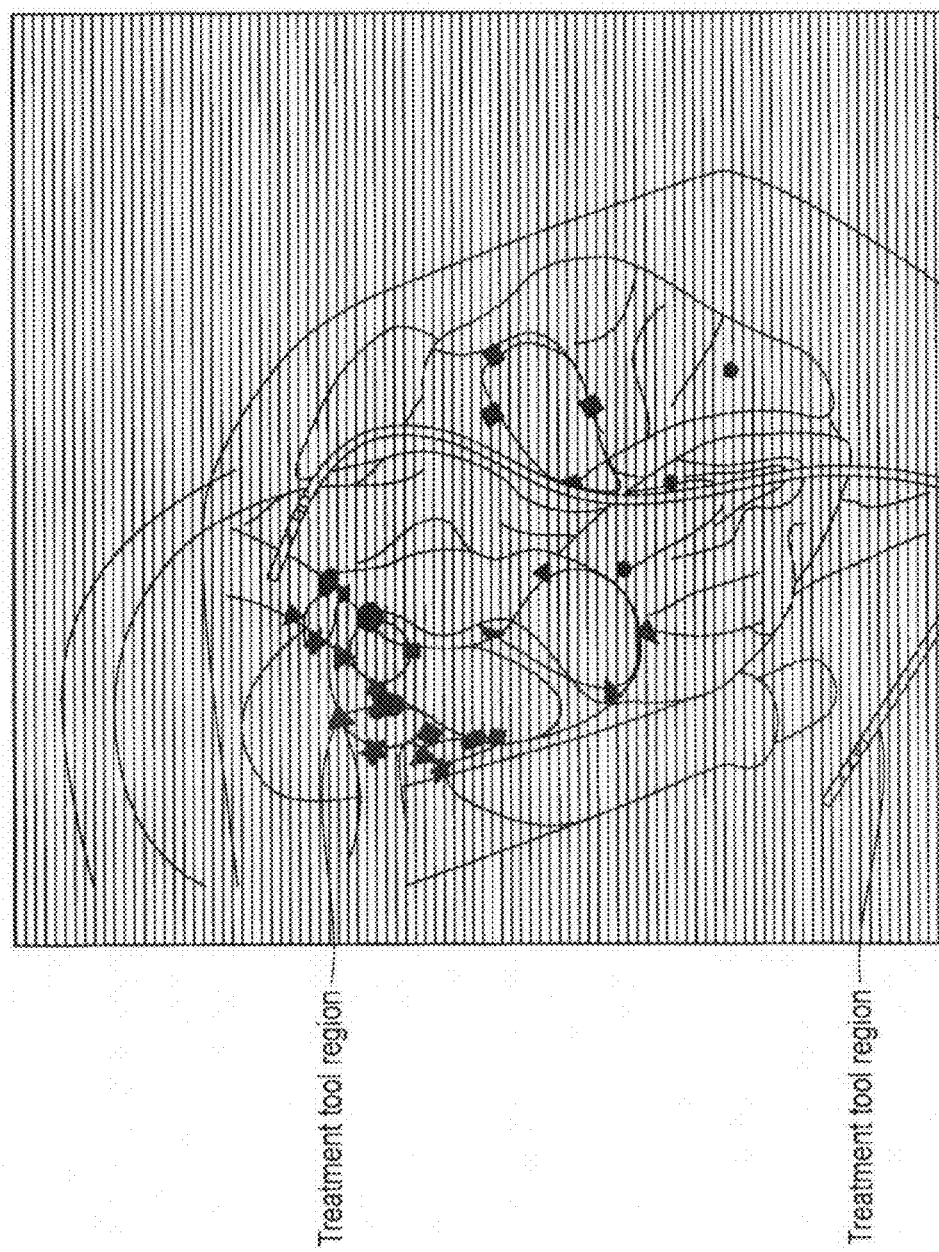
FIG. 3 is a view showing an example of an X-ray image generated by an X-ray image generation unit in FIG. 2.

FIG. 3 is a view showing an example of the X-ray image generated by the X-ray image generation unit 10 in FIG. 2 and containing electromagnetic field noise. As shown in FIG. 3, the X-ray image generated in the catheter ablation treatment depicts image regions (to be referred to as a treatment tool regions hereinafter) originating from a treatment tools such as an electrode catheter or wire. Electromagnetic field noise degrades the visibility of the treatment tool region. This makes it impossible for the operator to clearly grasp the position of the treatment tools.

Electromagnetic field noise has distinctive noise characteristics. More specifically, in the case shown in FIG. 3, electromagnetic field noise is depicted on an X-ray image as striped artifacts arrayed in the vertical direction. The noise characteristics of electromagnetic field noise are classified into image characteristics and frequency characteristics. Image characteristics are the properties of electromagnetic field noise, in an image space, which is depicted on an X-ray image. Image characteristics include the array direction and array pitch of striped artifacts. An array pitch is the inter-center distance between adjacent striped artifacts. Frequency characteristics are the properties of electromagnetic field noise in a frequency space. Frequency characteristics include a frequency axis (to be referred to as a noise frequency axis hereinafter) along which electromagnetic field noise components exist and a frequency range (to be referred to as a noise existence range hereinafter) where electromagnetic field noise components on the noise frequency axis exist. Image characteristics and frequency characteristics are not independent but correlated with each other. For example, the array direction of striped artifacts depends on the direction of a noise frequency axis. In addition, the array pitch of striped artifacts depends on a noise existence range. Note that the array direction of the striped artifacts in FIG. 3 is the vertical direction of the X-ray image. However, the array direction may be the horizontal direction. An image pattern of electromagnetic field noise depends on, for example, pixel pitch of the X-ray detector 7 or the readout method.

The X-ray diagnostic apparatus 1 according to this embodiment performs electromagnetic field noise reduction processing by using the above distinctive noise characteristics.

Figure 4:
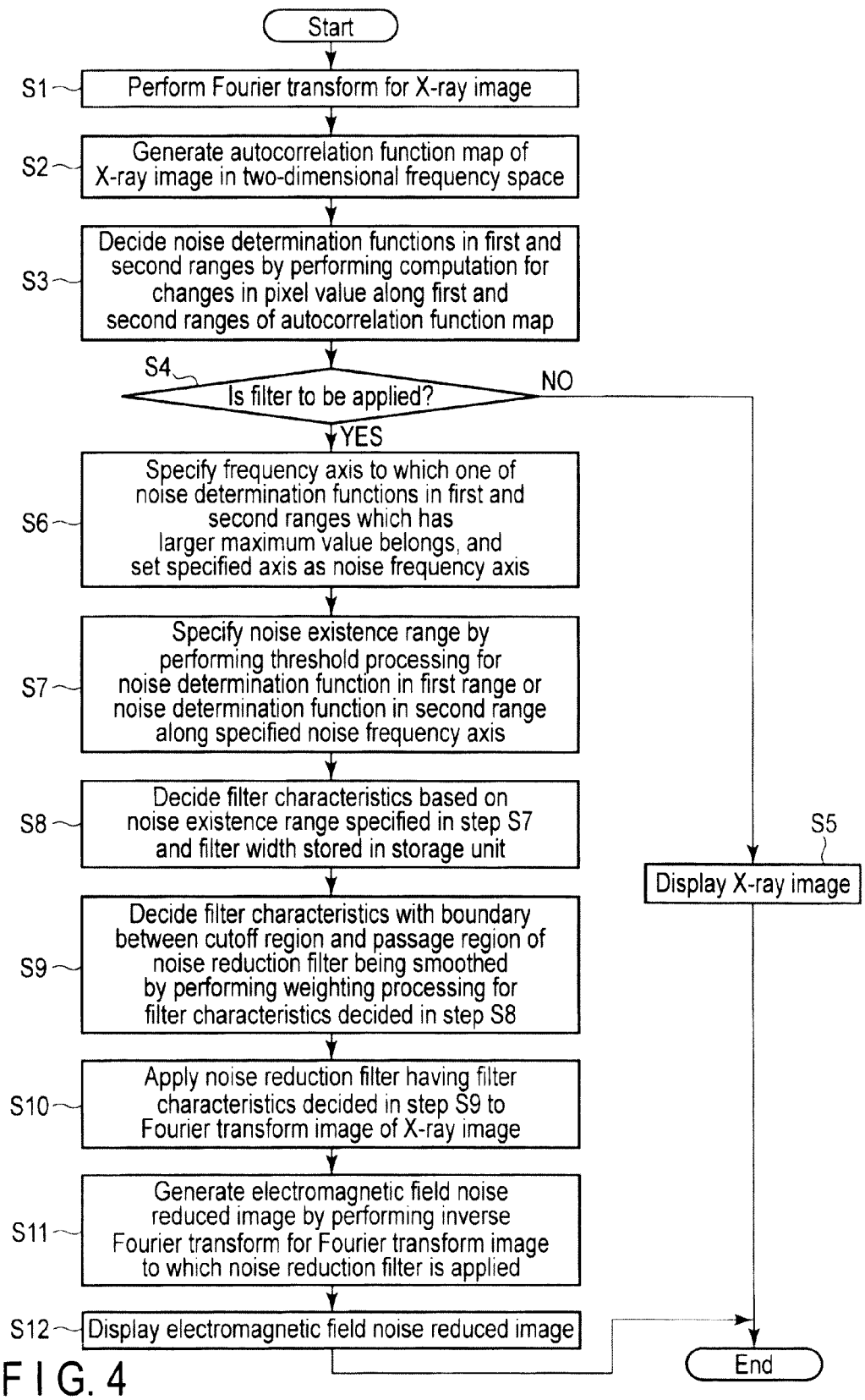
FIG. 4 is a flowchart schematically showing a typical procedure for electromagnetic field noise reduction processing performed under the control of a system control unit in FIG. 2.

Electromagnetic field noise reduction processing will be described below with reference to FIG. 4. FIG. 4 is a flowchart schematically showing a typical procedure for electromagnetic field noise reduction processing performed under the control of the system control unit 29 according to this embodiment.

Assume that electromagnetic field noise reduction processing according to this embodiment is performed under X-ray fluoroscopy. When performing X-ray fluoroscopy, the X-ray tube 5 continuously or intermittently generates X-rays under the control of the X-ray control unit 11. The X-ray detector 7 repeatedly detects X-rays generated by the X-ray tube 5. The X-ray image generation unit 10 repeatedly generates X-ray images based on the digital data output from the X-ray detector 7. The following electromagnetic field noise reduction processing is performed for each of a plurality of X-ray images generated by the X-ray image generation unit 10 under the control of the system control unit 29.

Figure 5:
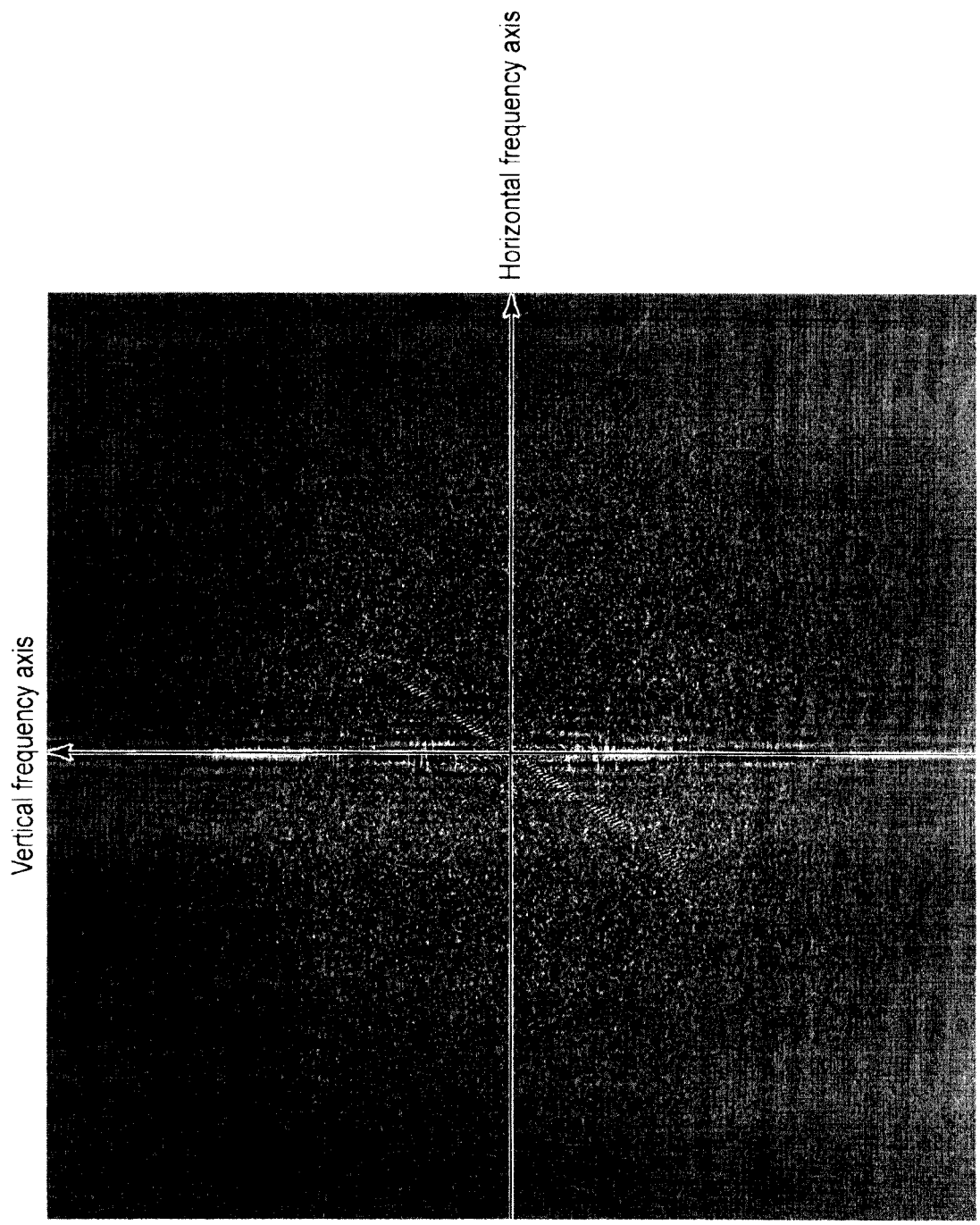
FIG. 5 is a view showing an example of a Fourier transform image of a real part generated by a specifying unit in FIG. 2.
Figure 6:
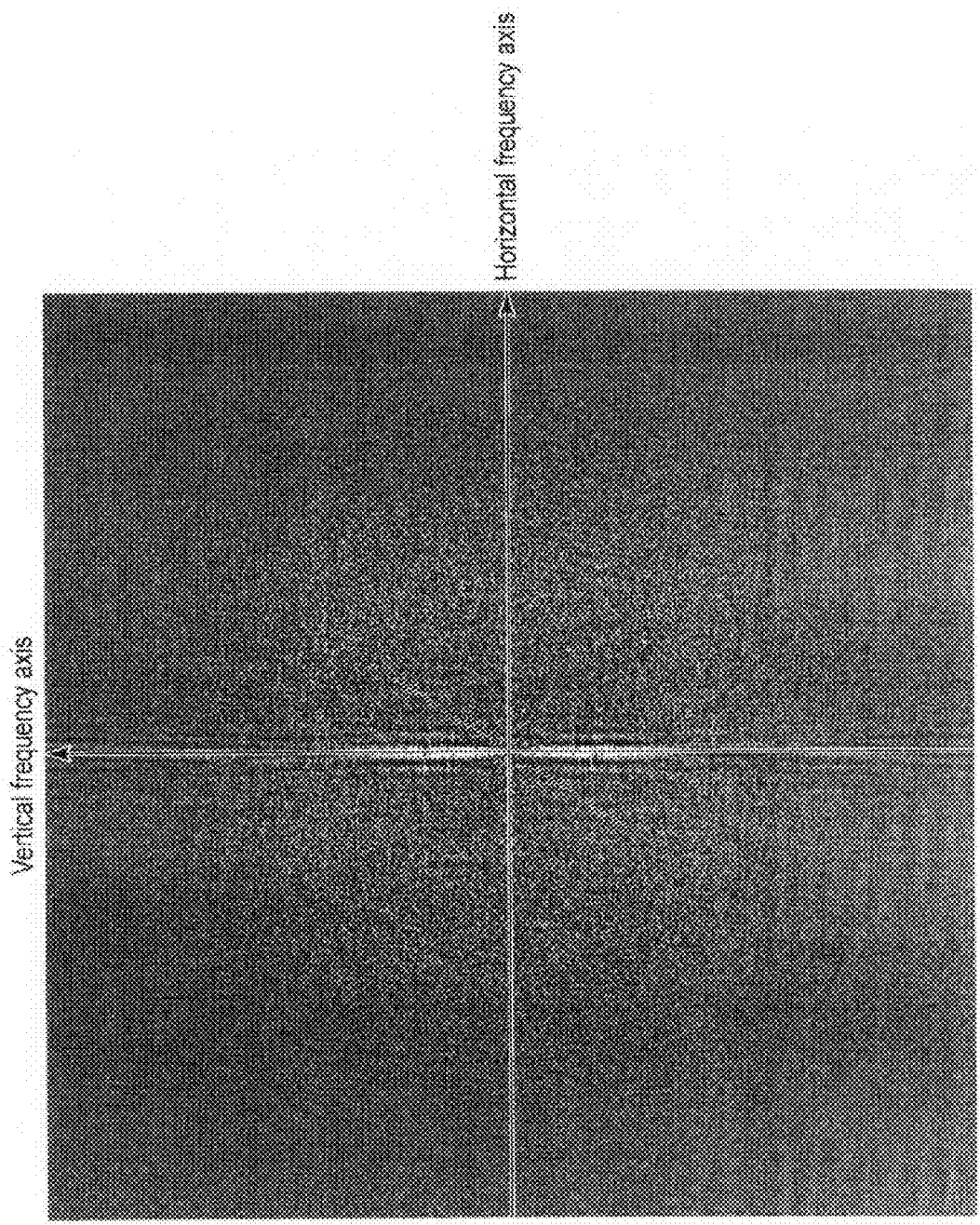
FIG. 6 is a view showing an example of a Fourier transform image of an imaginary part generated by the specifying unit in FIG. 2.

First of all, the system control unit 29 causes the specifying unit 21 to Fourier-transform an X-ray image (step S1). In step S1, the specifying unit 21 generates a Fourier transform image by Fourier-transforming the X-ray image. The Fourier transform image includes a Fourier transform image of a real part and a Fourier transform image of an imaginary part. FIG. 5 is a view showing an example of the Fourier transform image of the real part generated by the specifying unit 21 in FIG. 2. FIG. 6 is a view showing an example of the Fourier transform image of the imaginary part generated by the specifying unit 21 in FIG. 2. FIGS. 5 and 6 represent the pixel values of the respective images by color gradation.

Figure 7:
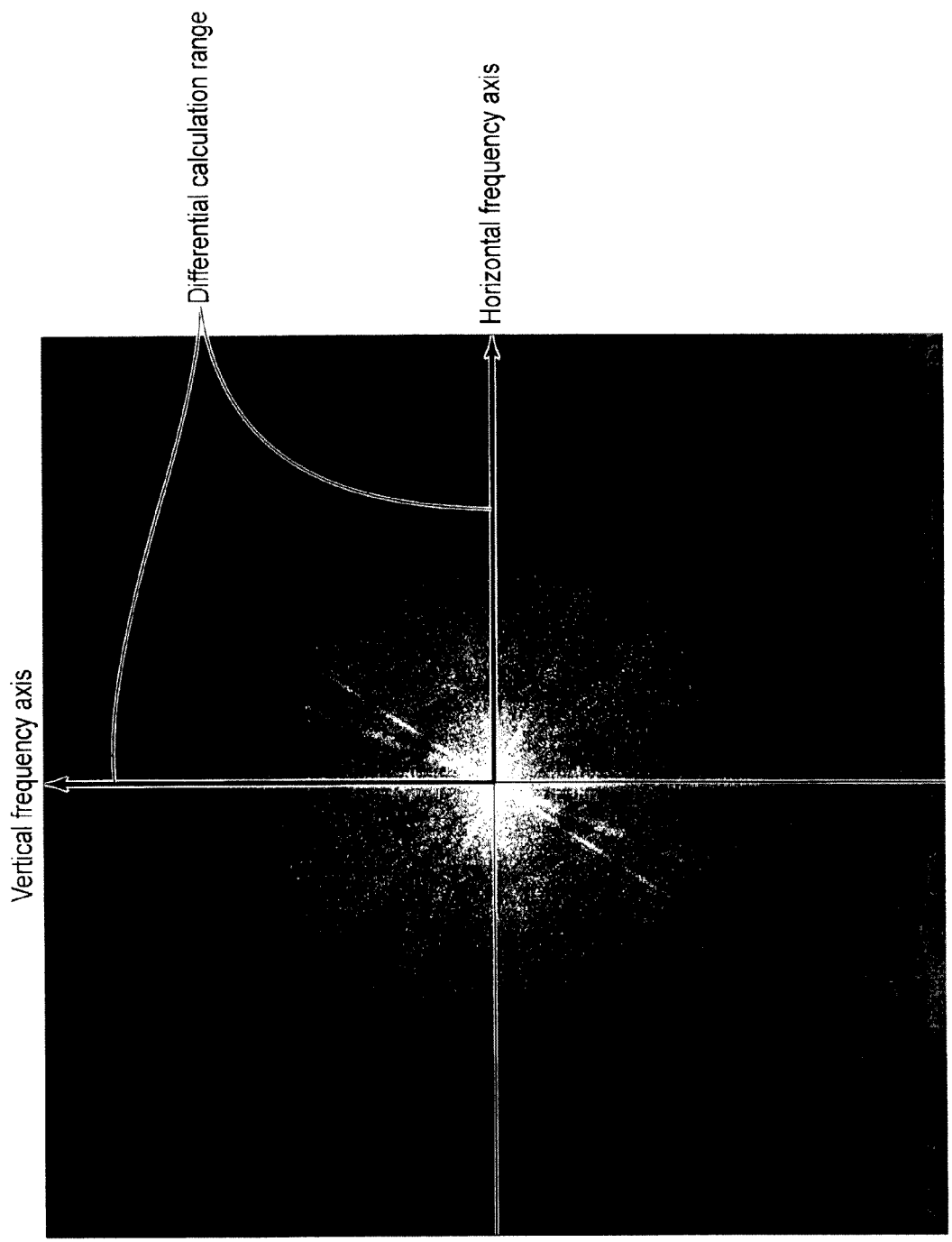
FIG. 7 is a view showing an example of an autocorrelation function map of an X-ray image in a two-dimensional frequency space which is generated by the specifying unit in FIG. 2.

Upon performing step S1, the system control unit 29 causes the specifying unit 21 to generate the autocorrelation function map of an X-ray image in a two-dimensional frequency space (step S2). In step S2, the specifying unit 21 calculates the squares of the pixel values of the Fourier transform image of the real part obtained in step S1. The specifying unit 21 squares the pixel values of the Fourier transform image of the imaginary part obtained in step S1. The specifying unit 21 generates an autocorrelation function map of an X-ray image in a two-dimensional frequency space by adding the squared values of the Fourier transform images of the real and imaginary parts at the respective points in the two-dimensional frequency space. FIG. 7 is a view showing an example of the autocorrelation function map of the X-ray image in the two-dimensional frequency space, which is generated by the specifying unit 21 in FIG.

2. FIG. 7 represents pixel values by color gradation. Note that the matrix size of the autocorrelation function map may be the same as that of the X-ray image or limited within a differential calculation range. In this case, a differential calculation range is a calculation range used for computation processing for specifying noise characteristics in steps S3 to S7. A differential calculation range is constituted by a differential calculation range on a horizontal frequency axis and a differential calculation range on a vertical frequency axis. In order to give a concrete description below, assume that the differential calculation range on the horizontal frequency axis is the range defined by 0 or more and a predetermined value or less on the horizontal frequency axis, as shown in FIG. 7. The predetermined value is, for example, the value obtained by dividing the X-ray image matrix size in the horizontal direction by 2. Assume that the differential calculation range on the vertical frequency axis is the range defined by 0 or more and a predetermined value or less on the vertical frequency axis, as shown in FIG. 7. The predetermined value is, for example, the value obtained by dividing the X-ray image matrix size in the vertical direction by 2. In order to give a concrete description below, assume that the X-ray image matrix size in the horizontal direction is equal to that in the vertical direction. That is, the differential calculation range on the horizontal frequency axis is equal to that on the vertical frequency axis.

Upon performing step S2, the system control unit 29 causes the specifying unit 21 to decide functions (to be referred to as noise determination functions hereinafter) for determining noise in the first and second ranges (step S3). In this case, the first and second ranges each are defined by the lower limit frequency stored in the storage unit 28. The first and second ranges are ranges each defined by the lower limit frequency or more and a predetermined value or less. The predetermined value is, for example, the value obtained by dividing the matrix size by 2. Note that the lower limit frequency is set to exclude a frequency range near a frequency of 0 which includes signal components of the image more than noise components from targets to be cut off by the noise reduction filter (to be described later), thereby preventing reductions in amplitude at frequencies near a frequency of 0. More specifically, the lower limit frequency is preferably set to a positive number which is larger than a value in the frequency range near a frequency of 0 which includes signal components of the image more than noise components and smaller than a predetermined value. The first and second ranges are used to determine noise and specify noise characteristics in steps S3 to S7.

In step S3, the specifying unit 21 decides a noise determination function in the first range by performing computation for a pixel value change along the first range on the autocorrelation function map. The specifying unit 21 decides a noise determination function in the second range by performing computation for a pixel value change along the second range on the autocorrelation function map. FIG. 8 is a graph showing an example of noise determination functions in the first and second ranges, which are generated by the specifying unit 21 in FIG. 2. The value of the noise determination function in the first range is the absolute value of a differential value of a pixel value change along the first range on the autocorrelation function map with respect to a horizontal frequency. The value of the noise determination function in the second range is the absolute value of a differential value of a pixel value change along the second range on the autocorrelation function map with respect to a vertical frequency.

Upon performing step S3, the system control unit 29 causes the determination unit 22 to determine whether to apply the noise reduction filter to an X-ray image (step S4). In step S4, the determination unit 22 determines whether to apply the noise reduction filter to the X-ray image, based on the maximum value of the noise determination function in the first range and the maximum value of the noise determination function in the second range. The determination unit 22 decides the quotient obtained by dividing a larger one of the maximum value of the noise determination function in the first range and the maximum value of the noise determination function in the second range by the other value (the smaller value). In the case shown in FIG. 8, the noise determination function in the second range has the maximum value shown in FIG. 8. On the other hand, the noise determination function in the first range remains almost 0, and the maximum value is also almost 0. That is, referring to FIG. 8, the maximum value of the noise determination function in the second range is larger than that of the noise determination function in the first range. Therefore, the determination unit 22 decides the quotient obtained by dividing the maximum value of the noise determination function in the second range by the maximum value of the noise determination function in the first range. When the decided quotient is large, it indicates that a strong noise component exists in one of the first and second ranges. In this case, the strong noise component existing in one of the first and second ranges is electromagnetic field. Performing determination processing for the decided quotient will determine whether electromagnetic field exists. Determining whether electromagnetic field noise exists will determine whether to apply the noise reduction filter. More specifically, if the quotient is larger than the determination constant, the determination unit 22 determines to apply the noise reduction filter. If the quotient is smaller than the determination constant, the determination unit 22 determines not to apply the noise reduction filter. If the determination unit 22 determines not to apply the noise reduction filter, the process advances to step S5.

If the determination unit 22 determines in step S4 not to apply the noise reduction filter, the system control unit 29 causes the display unit 26 to display the X-ray image (step S5).

If the determination unit 22 determines in step S4 to apply the noise reduction filter, the system control unit 29 causes the specifying unit 21 to specify a specific frequency axis (noise frequency axis) on which electromagnetic field noise exists (step S6). In step S6, the specifying unit 21 specifies a noise frequency axis based on the noise determination function in the first range and the noise determination function in the second range. More specifically, the specifying unit 21 specifies a frequency axis to which one of the noise determination function in the first range and the noise determination function in the second range which has a larger maximum value belongs. The specifying unit 21 sets the specified axis as a noise frequency axis. In order to give a concrete description below, assume that the vertical frequency axis is set as a noise frequency axis. In this case, the existence of noise components on the horizontal frequency axis indicates that striped noise arrayed in the horizontal direction on the X-ray image exists. The existence of noise components on the vertical frequency axis indicates that striped noise arrayed in the vertical direction on the X-ray image exists. Specifying a noise frequency axis in step S6 can specify that the array direction of striped noise on an X-ray image is vertical or horizontal.

Figure 9:
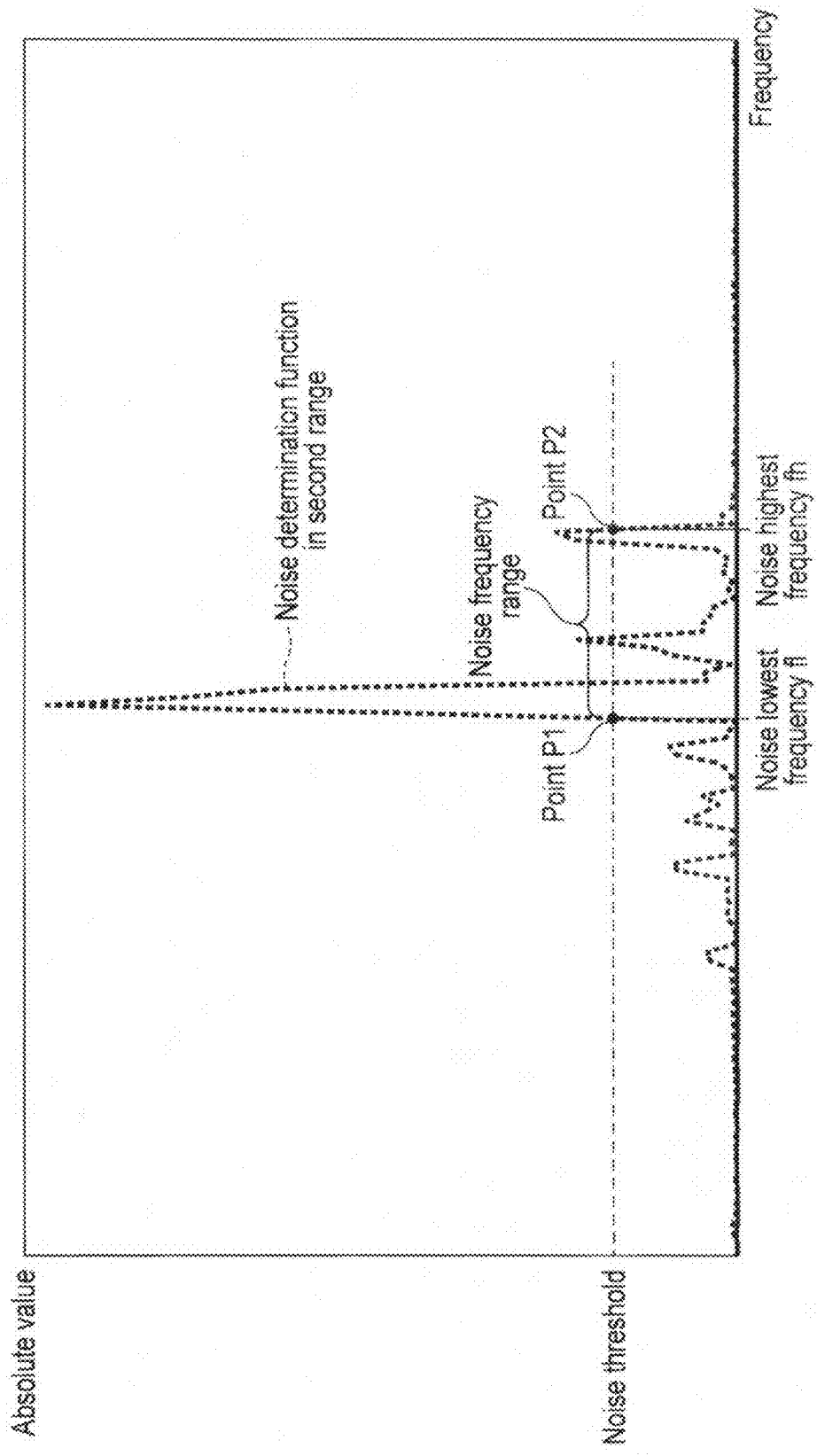
FIG. 9 is a graph for explaining how the specifying unit in FIG. 2 specifies a noise existence range.

Upon performing step S6, the system control unit 29 causes the specifying unit 21 to specify a specific frequency range (noise existence range) where noise components exist (step S7). In step S7, the specifying unit 21 specifies a noise existence range by performing threshold processing for a noise determination function along the noise frequency axis specified in step S6. Note that threshold processing need not be performed for all ranges on the noise frequency axis specified in step S6. Threshold processing may be performed for one of the first and second ranges belonging to the noise frequency axis specified in step S6. FIG. 9 is a graph for explaining how a noise existence range is specified. FIG. 9 is an enlarged view of part of FIG. 8. The specifying unit 21 decides a point P1, of a plurality of points constituting a noise determination function in the second range on the vertical frequency axis, which exhibits an absolute value larger than the noise threshold and the lowest frequency. The specifying unit 21 specifies the frequency at the point P1 as a lowest frequency fl. The specifying unit 21 decides a point P2, of the plurality of points constituting a noise determination function in the second range on the vertical frequency axis, which exhibits an absolute value larger than the noise threshold and the highest frequency. The specifying unit 21 specifies the frequency at the point P2 as a highest frequency fh. The specifying unit 21 sets the frequency range between the decided lowest frequency fl or more and the highest frequency fh or less as a noise existence range. Note that the noise existence range includes frequency ranges of positive and negative values whose absolute values are equal to each other. In step S7, the noise existence range corresponds to the array pitch of striped noise components on the X-ray image.

There has been described the manner of specifying frequency characteristics as noise characteristics unique to noise components. However, the specifying unit 21 may specify an image pattern as noise characteristics unique to noise components by image processing in an image space instead of steps S1 to S7 described above.

Upon performing step S7, the system control unit 29 causes the decision unit 23 to decide filter characteristics (step S8). In step S8, the decision unit 23 decides filter characteristics based on the noise characteristics specified in step S7. The decision unit 23 decides filter characteristics based on the noise existence range specified in step S7 and the filter width stored in the storage unit 28.

FIG. 10 is a view showing an example of a noise reduction filter having filter characteristics decided by the decision unit 23 in step S8. The above noise reduction filter has a cutoff region R1 and a passage region R2. Frequency components belonging to the cutoff region R1 are removed. Frequency components belonging to the passage region R2 are maintained. Applying the above noise reduction filter to the Fourier transform of an X-ray image can cut off frequency components in the cutoff region of the X-ray image. The frequency range of the cutoff region R1 in the vertical direction is set to the noise existence range specified in step S7. The frequency range of the cutoff region R1 in the horizontal direction is set to the filter width stored in the storage unit 28.

Upon performing step S8, the system control unit 29 causes the decision unit 23 to adjust the filter characteristics (step S9). In step S9, the decision unit 23 smooths the boundary between the cutoff region R1 and the passage region R2 by performing weighting processing for the filter characteristics decided in step S8. FIG. 11 is a view showing an example of the noise reduction filter which is generated by the decision unit 23 in step S9, with the boundary between the cutoff region R1 and the passage region R2 being smoothed. Smoothing the boundary between the cutoff region R1 and the passage region R2 can reduce artifacts on the electromagnetic field noise reduced image generated by the noise-reduced image generation unit 24 (to be described later). The above artifacts are caused by the sharpness of the boundary between the cutoff region and the passage region. Note that if there is no need to reduce the above artifacts, it is not always necessary to decide filter characteristics in step S9.

Upon performing step S9, the system control unit 29 causes the noise-reduced image generation unit 24 to apply the noise reduction filter decided in step S9 to the Fourier transform image (step S10). Applying the noise reduction filter to the Fourier transform image will reduce noise components belonging to the noise existence range contained in the Fourier transform image.

Upon performing step S10, the system control unit 29 causes the noise-reduced image generation unit 24 to generate an electromagnetic field noise reduced image (step S11). In step S10, the noise-reduced image generation unit 24 generates an electromagnetic field noise reduced image by applying an inverse Fourier transform to the Fourier transform image to which the noise reduction filter has been applied.

Figure 12:
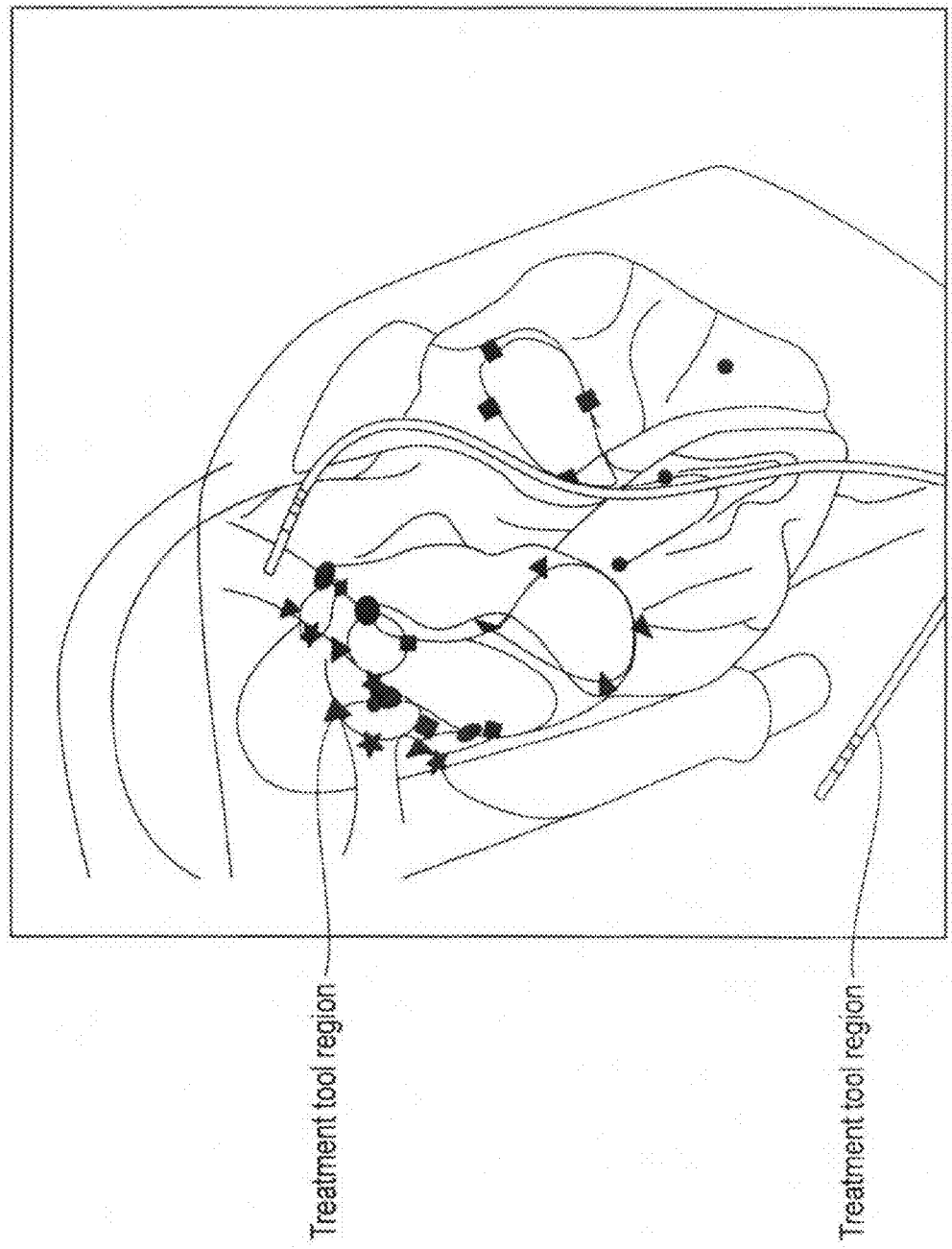
FIG. 12 is a view showing an example of the electromagnetic field noise reduced image generated by the generation unit in FIG. 2.

Upon performing step S11, the system control unit 29 causes the display unit 26 to display the electromagnetic field noise reduced image (step S12). FIG. 12 is a view showing an example of the electromagnetic field noise reduced image generated by the noise-reduced image generation unit 24 in step S11. In other words, the electromagnetic field noise reduced image in FIG. 12 is the image obtained by performing electromagnetic field noise reduction processing for the X-ray image in FIG. 3. As shown in FIG. 12, the electromagnetic field noise contained in the X-ray image before the application of the filter is not contained in the electromagnetic field noise reduced image. As is apparent from a comparison between FIGS. 12 and 3, the striped electromagnetic field noise is removed from the electromagnetic field noise reduced image.

According to the above operation example, a noise reduction filter is decided for each generated X-ray image and applied to the image. However, a noise reduction filter need not always be applied to an X-ray image used for the decision of the noise reduction filter. That is, the noise reduction filter may be applied to an X-ray image generated after the X-ray image used for the decision of the noise reduction filter. When the noise reduction filter is applied to the X-ray image generated after the X-ray image used for the decision of the noise reduction filter, the waiting time for the application of the noise reduction filter is shortened as compared with the case in which a noise reduction filter is applied to an X-ray image used for the decision of the noise reduction filter. That is, the real-time performance of noise reduction processing improves.

In addition, a noise reduction filter need not be decided based on each generated X-ray image. More specifically, the noise reduction filter decided based on a given X-ray image can be applied or determined to be applied to a predetermined number of consecutively generated X-ray images. For example, the noise reduction filter decided based on a given X-ray image may be applied to X-ray images corresponding to five frames. More specifically, a noise reduction filter is decided based on the X-ray image generated first, and is applied to X-ray images generated first to fifth. A noise reduction filter is decided based on an X-ray image generated sixth, and is applied to X-ray images generated sixth to 10th. In this case, the number of noise reduction filters to be decided is reduced to ⅕. This shortens the time required to decide noise reduction filters and improves the real-time performance of noise reduction processing. If it is determined by filter application determination processing that no noise reduction filter is applied to a given X-ray image, no noise reduction filter may be applied. Referring to the above case, if it is determined that no noise reduction filter is applied to the X-ray image generated third, a noise reduction filter is decided based on the X-ray image generated first and is applied to the X-ray images generated first, second, fourth and fifth.

As described above, the X-ray image processing apparatus 4 according to this embodiment specifies noise characteristics unique to electromagnetic field, and decides a noise reduction filter having filter characteristics corresponding to the specified noise characteristics. That is, a noise reduction filter has filter characteristics unique to the electromagnetic field contained in an X-ray image as an application target. When such a noise reduction filter is applied to an X-ray image, the noise reduction filter can remove electromagnetic field noise without influencing treatment tool regions contained in the X-ray image. Therefore, the operator can clearly visually recognize the treatment tool region in the electromagnetic field noise reduced image, and can accurately grasp the position of the treatment tools.

In addition, the X-ray image processing apparatus 4 according to this embodiment can save unnecessary noise reduction processing by determining whether to apply a noise reduction filter to each captured X-ray image. If it is determined by electromagnetic field noise determination processing that almost no electromagnetic field exists on an X-ray image, no noise reduction filter is applied to the X-ray image. This shortens the time associated with a noise reduction filter, and improves the real-time performance of noise reduction processing.

The X-ray image processing apparatus 4 according to this embodiment, therefore, can improve the technical efficiency of a catheter ablation treatment.

Modifications of this embodiment will be described next.

First Modification

In the above embodiment, the X-ray image processing apparatus 4 decides a noise reduction filter by specifying noise characteristics for each X-ray image. More specifically, the X-ray image processing apparatus 4 specifies the noise characteristics of electromagnetic field noise contained in each X-ray image generated by X-ray fluoroscopy for each X-ray image, decides filter characteristics corresponding to the specified noise characteristics, and applies a noise reduction filter having the decided filter characteristics to the X-ray image. In other words, an X-ray image for specifying noise characteristics is the same as that of an application target of a noise reduction filter. However, this embodiment is not limited to this. The X-ray image processing apparatus 4 according to the first modification decides filter characteristics by using the specified noise characteristics based on one X-ray image, and applies a noise reduction filter having the decided filter characteristics to a plurality of X-ray images. In other words, according to the first modification, an X-ray image for specifying noise characteristics need not be the same as an X-ray image which is an application target of a noise reduction filter. An example of the operation of the X-ray image processing apparatus 4 according to the first modification will be described below.

The X-ray image processing apparatus 4 according to the first modification performs X-ray imaging or X-ray fluoroscopy in advance to generate an X-ray image (to be referred to as a dark image hereinafter) for the execution of noise characteristic specifying processing for electromagnetic field noise before the start of X-ray fluoroscopy under the action of the electromagnetic field generated from the mapping system 2. Since the dark image is only required to depict electromagnetic field noise, it is not always necessary to perform X-ray imaging or X-ray fluoroscopy for an object as an imaging object in advance. As in the above embodiment, the noise characteristics of electromagnetic field noise contained in the dark image are specified based on the generated dark image, and the filter characteristics of a noise reduction filter corresponding to the specified noise characteristics are decided. The decided filter characteristics are stored in the storage unit 28.

After the start of X-ray fluoroscopy, X-ray fluoroscopy is performed under the control of the system control unit 29. The X-ray image generation unit 10 repeatedly generates X-ray images. The noise-reduced image generation unit 24 reads out the filter characteristics stored in the storage unit 28. The noise-reduced image generation unit 24 performs a Fourier transform for each X-ray image generated by the X-ray image generation unit 10 to generate a Fourier transform image. The noise-reduced image generation unit 24 applies a noise reduction filter having the readout filter characteristics to each Fourier transform image.

As described above, the X-ray image processing apparatus 4 according to the first modification decides a noise reduction filter before the start of X-ray fluoroscopy. This makes it possible to reduce the amount of calculation for image processing at the time of X-ray fluoroscopy.

Second Modification

The X-ray image processing apparatus 4 according to the first modification applies a noise reduction filter to a Fourier transform image in a two-dimensional frequency space and then performs an inverse Fourier transform for the image to generate an electromagnetic field noise reduced image. However, this embodiment is not limited to this. The X-ray image processing apparatus 4 according to the second modification performs an inverse Fourier transform for a noise reduction filter and applies a noise reduction filter to an X-ray image in a real space. An example of the operation of the X-ray image processing apparatus 4 according to the second modification will be described below.

In the second modification, the decision unit 23 generates a real space filter by performing an inverse Fourier transform for the noise reduction filter decided based on the dark image generated by X-ray imaging or X-ray fluoroscopy in advance.

After the start of X-ray fluoroscopy, X-ray fluoroscopy is performed under the control of the system control unit 29. The X-ray image generation unit 10 repeatedly generates an X-ray image under X-ray fluoroscopy. The noise-reduced image generation unit 24 generates an electromagnetic field noise reduced image by performing convolution integration for each X-ray image by using the real space filter decided by the decision unit 23 in advance.

Figure 13:
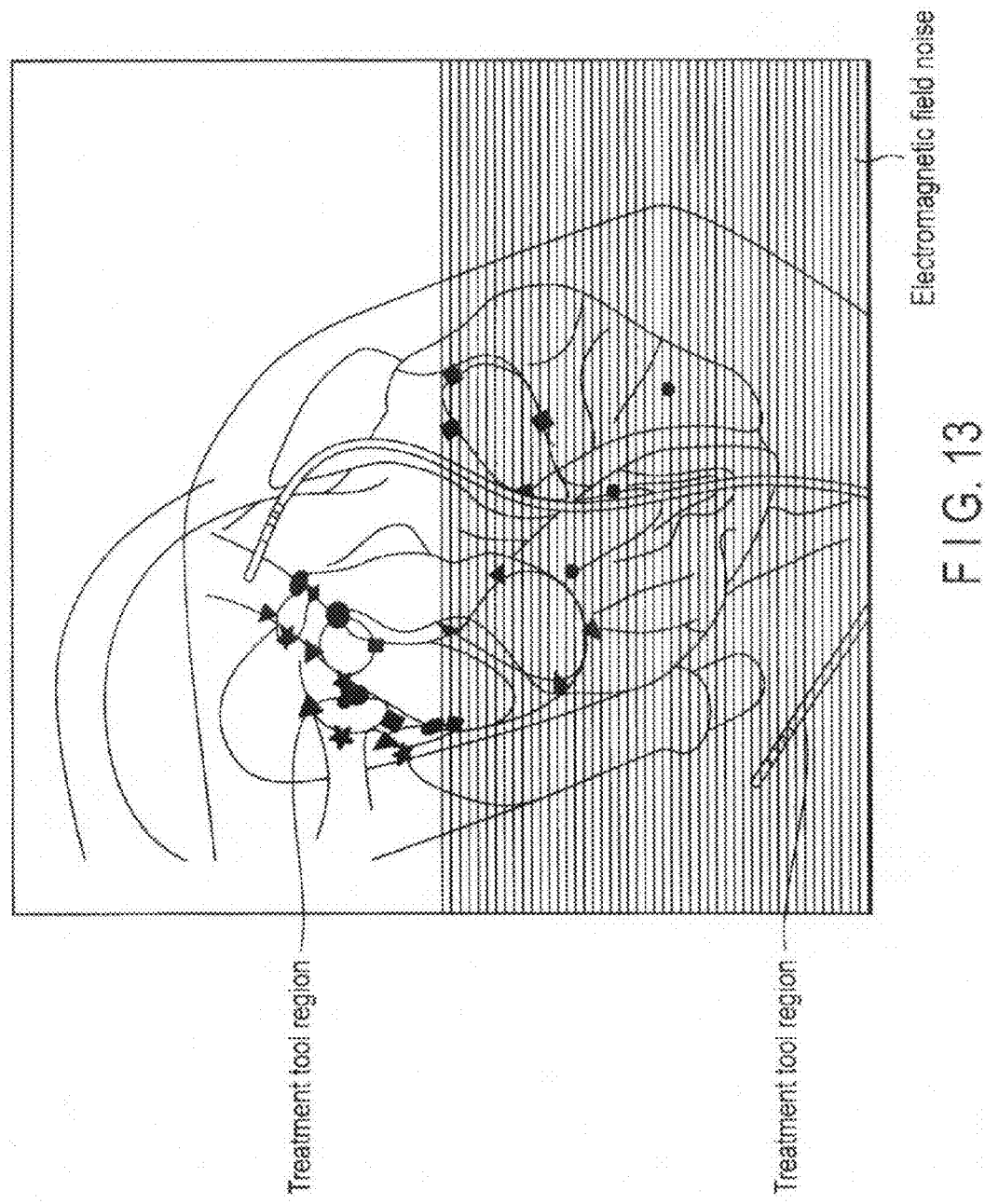
FIG. 13 is a view showing an example of an electromagnetic field noise reduced image according to the second modification.

FIG. 13 is a view showing an example of an electromagnetic field noise reduced image according to the second modification. When all the pixels constituting one X-ray image are displayed on the display unit 26, a noise reduction filter is applied to almost the upper half of the entire image to reduce electromagnetic field noise.

As described above, the X-ray image processing apparatus 4 according to the second modification performs an inverse Fourier transform for a noise reduction filter and applies the real space filter to an X-ray image in a real space. Even if one entire X-ray image is not acquired, it is possible to start applying a real space filter. As compared with the first modification, it is possible to quickly finish applying a noise reduction filter and implement the application of the real-time noise reduction filter.

According to the above description, electromagnetic field noise reduction processing according to this embodiment is performed under X-ray fluoroscopy. However, electromagnetic field noise reduction processing according to this embodiment may be performed under X-ray imaging.

As described above, the X-ray diagnostic apparatus according to this embodiment specifies, by image processing, noise characteristics unique to noise components on an X-ray image generated by an electromagnetic field generated by the mapping system 2. A filter for reducing the above noise components is decided based on the specified noise characteristics. Applying the decided noise reduction filter to the X-ray image can generate an electromagnetic field noise reduced image.

This embodiment can therefore provide an X-ray image processing apparatus, an X-ray diagnostic apparatus, and an X-ray image processing method which can reduce noise on an X-ray image which is generated by the mapping system 2 which executes the mapping method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray image processing apparatus comprising:
   processor circuitry:
      configured to perform frequency analysis on a first X-ray image based on an output signal from an X-ray detector influenced by an action of an electromagnetic field and specify, as a noise characteristic, a specific frequency axis and a specific frequency range where noise components originating from the action of the electromagnetic field on the X-ray detector and contained in the first X-ray image exist; and
      configured to decide a filter characteristic for reducing the noise components contained in the first X-ray image based on the noise characteristic in the first X-ray image; and
   a filter configured to perform filter processing for at least one of the first X-ray image and a second X-ray image generated after the first X-ray image, based on the filter characteristic,
   wherein the processor circuitry is further configured to generate from the first X-ray image a two-dimensional data in a two-dimensional frequency space constituted by a horizontal frequency axis and a vertical frequency axis, specify the specific frequency axis based on a pixel value change in a first range on the horizontal frequency axis and a pixel value change in a second range on the vertical frequency axis, and specify the specific frequency range by performing threshold processing for a pixel value change along the specific frequency axis.

2. The apparatus of claim 1, wherein the processor circuitry is further configured to:
   determine whether to apply a filter to the X-ray image, based on the specified noise characteristic,
   decide the filter characteristic if the determination unit decides to apply the filter, and
   not decide the filter characteristic if the determination unit determines not to apply the filter.

3. The apparatus of claim 1, wherein the first range and the second range are decided in accordance with a matrix size and a predetermined value of the first X-ray image.

4. The apparatus of claim 1, wherein the processor circuitry is further configured to specify, as the noise characteristic, an image pattern including an array direction of the noise components on the first X-ray image by processing the first X-ray image.

5. The apparatus of claim 2, wherein the processor circuitry is further configured to decide a filter characteristic defined in a frequency space based on the specified frequency axis and the specified frequency range.

6. The apparatus of claim 5, wherein a noise reduction filter having the filter characteristic includes a cutoff region which cuts off a signal in a corresponding frequency region and a passage region which passes a signal in a corresponding frequency region, and
   wherein the processor circuitry is further configured to smooth a boundary between the cutoff region and the passage region of the noise reduction filter by performing weighting processing for the noise reduction filter.

7. An X-ray image processing apparatus comprising:
   processor circuitry:
      configured to perform frequency analysis on a first X-ray image based on an output signal from an X-ray detector influenced by an action of an electromagnetic field and specify, as a noise characteristic, a specific frequency axis and a specific frequency range where noise components originating from the action of the electromagnetic field on the X-ray detector and contained in the first X-ray image exist;
      configured to decide a filter characteristic for reducing the noise components contained in the first X-ray image based on the noise characteristic in the first X-ray image;
   a filter configured to perform filter processing for at least one of the first X-ray image and a second X-ray image generated after the first X-ray image, based on the filter characteristic; and
   wherein the processor circuitry is further configured to generate a third X-ray image with noise components originating from an action of an electromagnetic field on the X-ray detector being reduced by applying a noise reduction filter having the decided filter characteristic to a second X-ray image as a noise reduction target,
   wherein the processor circuitry is further configured to apply the noise reduction filter to a Fourier transform image of the second X-ray image, and generates an X-ray image with the noise components reduced by performing an inverse Fourier transform for the Fourier transform image to which the noise reduction filter is applied.

8. The apparatus of claim 1, wherein the processor circuitry is further configured to:

generate a third X-ray image with noise components originating from an action of an electromagnetic field on the X-ray detector being reduced by applying a noise reduction filter having the decided filter characteristic to a second X-ray image as a noise reduction target, and apply a filter obtained by performing an inverse Fourier transform for the noise reduction filter to the second X-ray image.

9. The apparatus of claim 1, wherein the processor circuitry is further:

configured to generate a third X-ray image with noise components originating from an action of an electromagnetic field on the X-ray detector being reduced by applying a noise reduction filter having the decided filter characteristic to a second X-ray image as a noise reduction target; and further comprising a display configured to display the third X-ray image.

10. An X-ray diagnostic apparatus comprising:

an X-ray tube configured to generate X-rays;

an X-ray detector configured to detect the X-rays;

an image generator configured to generate a first X-ray image and a second X-ray image based on an output from the X-ray detector;

processor circuitry:

configured to perform frequency analysis on the first X-ray image based on the output signal from the X-ray detector influenced by an action of an electromagnetic field and specify, as a noise characteristic, a specific frequency axis and a specific frequency range where noise components originating from the action of the electromagnetic field on the X-ray detector and contained in the first X-ray image exist;

configured to decide a filter characteristic for reducing the noise components contained in the first X-ray image based on the noise characteristic in the first X-ray image; and a filter configured to perform filter processing for at least one of the first X-ray image and the second X-ray image generated after the first X-ray image, based on the filter characteristic, wherein the processor circuitry is further configured to generate from the first X-ray image a two-dimensional data in a two-dimensional frequency space constituted by a horizontal frequency axis and a vertical frequency axis, specify the specific frequency axis based on a pixel value change in a first range on the horizontal frequency axis and a pixel value change in a second range on the vertical frequency axis, and specify the specific frequency range by performing threshold processing for a pixel value change along the specific frequency axis.

11. The apparatus of claim 1, wherein the processing circuitry is further configured to generate the two-dimensional data by adding squared values of real and imaginary parts of a Fourier transform of the first X-ray image.

* * * * *